US007507553B2

(12) United States Patent
Park et al.

(10) Patent No.: US 7,507,553 B2
(45) Date of Patent: Mar. 24, 2009

(54) GALLERIA MELLONELLA DERIVED COMPOSITION FOR DETECTING PEPTIDOGLYCAN, A METHOD FOR USE THEREOF, AND A DIAGNOSTIC KIT CONTAINING THE SAME

(75) Inventors: Bu-Soo Park, Buk-Ku (KR); Bok-Luel Lee, Keumjeon-Ku (KR); Ji-Won Park, Nam-Ku (KR); Jeong-Mi Yeo, Bukcheju-Kun (KR); Hyun-Sic Kim, Suyong-Ku (KR); Chang-Hun Joo, Yuseong-Ku (KR); Moon-Suk Kim, Seo-Ku (KR); Seung-Hwan Song, Yongsan-Ku (KR); Jong-Won Yoon, Yuseong-Ku (KR); Yeon-Sung Park, Koyang (KR); Hong-Lak Kim, Yuseong-Ku (KR); Joong-Hyuck Auh, Kangnam-Ku (KR); Tae-Hoon Cho, Suwon (KR)

(73) Assignee: Samyan Genex Corporation, Seoul (KR)

( * ) Notice: Subject to any disclaimer, the term of this patent is extended or adjusted under 35 U.S.C. 154(b) by 288 days.

(21) Appl. No.: 11/460,406

(22) Filed: Jul. 27, 2006

(65) Prior Publication Data

US 2006/0292662 A1 Dec. 28, 2006

Related U.S. Application Data (63) Continuation-in-part of application No. 10/479,910, filed as application No. PCT/KR02/01086 on Jun. 7, 2001, now abandoned.

(30) Foreign Application Priority Data

| Jun. 8, 2001 | (KR) | ................... 2001-31890 |
| Jun. 7, 2002 | (KR) | ................... 2002-31856 |

(51) Int. Cl.
*C12Q 1/26* (2006.01)

(52) U.S. Cl. ........................ 435/25; 424/538

(58) Field of Classification Search ................ 435/25, 435/259; 424/538
See application file for complete search history.

(56) References Cited

U.S. PATENT DOCUMENTS

| 4,675,290 | A | | 6/1987 | Matsumoto et al. |
| 4,970,152 | A | * | 11/1990 | Ashida et al. ................ 435/19 |
| 5,585,248 | A | | 12/1996 | Ashida et al. |
| 5,747,277 | A | * | 5/1998 | Tsuchiya ..................... 435/34 |
| 6,274,565 | B1 | | 8/2001 | Katsumi |
| 6,306,577 | B1 | | 10/2001 | Tamura et al. |
| 2001/0052905 | A1 | | 12/2001 | O'Connor |
| 2002/0101083 | A1 | | 8/2002 | Toledano et al. |
| 2003/0113877 | A1 | | 6/2003 | Ohno et al. |

FOREIGN PATENT DOCUMENTS

| JP | 11178599 A2 | 7/1999 |
| JP | 11196885 A2 | 7/1999 |

OTHER PUBLICATIONS

Yoshida, H., et al Purification of a Peptidoglycan Recognition Protein from Hemolymph of the Silkworm *Bombyx mori*, J of Biological Chemistry 271(23) 13854-60, Jun. 1996.

Tsuchiya M., et al Detection of Peptidoglycan and Beta-Glucan with Silkworm Larvae Plasma Test. FEMS Immunology and Medical Microbiology 15(2-3) 129-134, 1996.

* cited by examiner

*Primary Examiner*—Ralph Gitomer
(74) *Attorney, Agent, or Firm*—Gifford, Krass, Sprinkle, Anderson & Citkowski, P.C.

(57) ABSTRACT

The present invention relates to a composition for selectively detecting an extremely small amount of peptidoglycan in sample, a preparation method of the composition, and a detection kit for peptidoglycan. It is possible to quantify a small amount of peptidoglycan contained in human blood, tissue, body fluid, water or food, and to diagnose an infection of microorganism with peptidoglycan as a component of cell wall using the composition and the detection kit. In addition, the composition can be applied for a diagnosis reagent of detecting an infection of Gram-positive bacteria in animal or human being in advance, and thus, can be used for the prevention or treatment of food poisonings and bacterial sepsis.

20 Claims, 8 Drawing Sheets

GALLERIA MELLONELLA DERIVED COMPOSITION FOR DETECTING PEPTIDOGLYCAN, A METHOD FOR USE THEREOF, AND A DIAGNOSTIC KIT CONTAINING THE SAME

CROSS REFERENCE TO RELATED APPLICATIONS

This application claims priority to and the benefit of U.S. patent application Ser. No. 10/479,910 filed Dec. 5, 2005 now abandoned; which in turn claims the benefit of PCT Application PCT/KR02/01086 filed Jun. 7, 2002; which in turn claims the benefit of Korean Application Nos. 10-2001-31890 and 10-2002-31856, filed on Jun. 8, 2001 and Jun. 7, 2002 in the Korean Intellectual Property Office, the entire disclosure of which are incorporated herein by reference.

BACKGROUND OF THE INVENTION (a) Field of the Invention

The present invention relates to a composition for detecting peptidoglycan, and a diagnostic kit for peptidoglycan using the same.

(b) Description of the Related Art

The infection of the pathogenic Gram-positive bacterium constitutes a large portion of widely-spread bacterial infection in hospitals. Food poisonings and bacterial sepsis caused by Gram-positive bacterium are lethal diseases. A rapid detecting system for Gram-positive bacteria in clinical samples such as blood, tissue, and urine, and food is necessary.

According to a conventional technique, it takes a few days to detect the bacteria. As foods contaminated with the bacteria will be distributed during this detection period, additional consumers may be infected.

It is possible to detect Gram-positive bacteria living in various types of samples in small amounts by detecting and quantifying the peptidoglycan.

The peptidoglycan is a kind of glycoprotein polymer constituting bacterial cell walls and contains N-acetylmuramic acid or N-glycosylmuramic acid and D-amino acid in outer cell wall of Gram-positive bacteria.

Accordingly, a detecting and measuring method of the peptidoglycan can be applied for testing the safeness of the medicine, detecting microorganism in food and water, and performing diagnosis of infectious disease.

It is reported that a prophenoloxydase system of insect can detect selectively a small amount of lipopolysaccharide (LPS), peptidoglycan, and beta-1,3-glucan, in which zymogen-type prophenoloxydase is converted to phenoloxidase in active form through cascade reactions to amplify the signal more than 1,000 times, However, the prophenoloxydase system detects all components including lipopolysaccharide, peptidoglycan, and beta-1,3-glucan. Therefore, a system for selectively detecting any one of them is necessary.

A prophenoloxidase, which exists in insect body with complete metamorphosis, is activated to phenoloxidase through cascade reaction on the beta-1,3-glucan or lipopolysaccharide. The prophenoloxidase reaction system consisting of a series of cascade reaction steps can be easily activated to phenoloxidase system to produce melanin by using catechol amines when it is exposed to exterior factors such as a pathogenic microorganism and materials, or interior factors derived from degranulation of interior hemocyte, etc. Thus, it is difficult to extract the prophenoloxidase system from the insect body (Ashida and Yoshida, (1988), Insect. Biochem. 18, 11-19).

Ashida et al. reported in Eur. J. Biochem, 188, 507-515 (1990) that bivalent ion plays an important role in activating prophenoloxidase system by introducing a composition which recognizes beta-1,3-glucan separated from mosquito larva, and disclosing that prophenoloxidase system of insects requires $Ca^{2+}$ for its activation.

A composition and method for detecting peptidoglycan was disclosed in U.S. Pat. No. 4,970,152 where a protein reacting with beta-1,3-glucan was removed from silkworm plasma to produce a reagent for specifically detecting a peptidoglycan. However, the addition of $Ca^{2+}$ or $Mg^{2+}$ is required for activating a phenoloxidase system on peptidoglycan. In other words, according to U.S. Pat. No. 4,970,152, inhibition of the phenoloxidase system activation by adding $Ca^{2+}$ is necessary when obtaining a phenoloxidase composition from the insect body fluid and triggering a color reaction on the peptidoglycan as a substrate with the composition.

Also, U.S. Pat. No. 5,747,277 disclosed a SLP reagent. However, this reagent detected beta-1,3-glucan and peptidoglycan at the same time; therefore, it did not show a specific reaction to only peptidoglycan. As result, this reagent cannot be used for the detection of only peptidoglycan. Additionally, the SLP reagent includes $Ca^{2+}$.

SUMMARY OF THE INVENTION

Considering the shortcomings of the prior arts, the present invention provides a composition for selectively detecting a peptidoglycan.

This invention also provides a preparation method of the composition for detecting peptidoglycan.

This invention further provides a method for selectively detecting peptidoglycan using the composition.

This present invention further still provides a detection kit for selectively detecting peptidoglycan using the composition.

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

The present invention is directed to a composition for detecting peptidoglycan in a sample, a preparation method of the composition, and a detection kit for detecting peptidoglycan using the same.

In the present invention, a phenoloxidase system is intended to mean a system which is in *Galleria mellonella* larvae, and can be activated and converted to phenoloxidase by peptidoglycan.

In the present invention, a phenoloxidase composition is intended to mean a composition which comprises parts of phenoloxidase system or whole phenoloxidase system, and has a phenoloxidase activity on peptidoglycan.

In the present invention, a phenoloxidase system of *Galleria mellonella* does not require Ca2+ for its activation. Moreover, the addition of Ca2+ causes the suppression of the phenoloxidase activity.

The present invention provides a composition for detecting a peptidoglycan comprising extract of insect body fluid which has a phenoloxidase activity on peptidoglycan without the addition of divalent cations, such as Ca2+, Mg2+, or other divalent cations. The extract of insect body fluid can be a plasma solution separated from insect body fluid. Compared with the composition containing only the plasma solution, the composition that further comprises hemocyte lysate in addition to the plasma solution allows detection of peptidoglycan that is small. In number despite smaller amount of plasma solution is used. Thus, the composition comprising the plasma solution and hemocyte lysate is preferred.

The composition comprising plasma solution of insect body fluid and hemocyte lysate can be prepared by separating or without separating the hemocyte. In other words, the composition comprising plasma solution of insect body fluid and hemocyte lysate can be prepared by separating the hemocyte from the body fluid, lysing the hemocyte, and then adding the hemocyte lysate to the plasma solution. Or, the hemocyte lysate or partially purified hemocyte lysate can be added to the partially purified plasma.

Alternatively, when the hemocyte contained in the body fluid is not separated, the hemocyte can be broken down in part or as a whole to produce the solution. For examples, the sonification or high-speed centrifugation can be carried out on the body fluid or separated hemocyte. Also, the plasma solution, hemocyte lysate, and their mixture can be used in diluted form with addition of buffer solution, or in concentrated form by conventional concentration method. In the present invention, the hemocyte is intended to mean precipitation which can be obtained by removing the plasma solution from the insect body fluid. The hemocyte lysate can be a lysate prepared by breaking down the hemocyte with addition of solvent, more preferably by obtaining supernatant form of the lysate.

In the composition for detecting peptidoglycan according to the present invention, the extract of insect body fluid is preferably derived from *Galleria mellonella* larvae. That is, the composition comprises a part or whole of phenoloxidase system of *Galleria mellonella*, e.g. prophenoloxidase system. *Galleria mellonella* is short-lived with a life span of two months more or less that is considerably shorter than most of other insects', and has strong multiplication capability allowing easy large-scale breeding means to yield a large amount of body fluid.

The plasma solution contained in insect body fluid can be obtained by treating *Galleria mellonella* larvae with solvent or buffer solution to produce factions, and by selecting the fraction showing a phenoloxidase activity on peptidoglycan without addition of Ca2+, Mg2+, or other divalent cations. Preferably, the solvent or buffer solution comprises sufficient amount of cheating agent to chelate Ca2+ in a sample or separation processes. More preferably, the fraction can be prepared by column chromatography. For example, the column can be filled with a sugar resin or vinyl resin as a carrier.

The composition for detecting peptidoglycan according to the present invention can be used for detecting the infection with Gram-positive bacteria, such as *Staphylococcus, Streptococcus, Pneumococcus,* and *Corynebacterium diphtheriae* in an individual.

In another aspect of the present invention, the preparation method of composition comprising extract of insect body fluid which shows a phenoloxidase activity on peptidoglycan without the addition of Ca2+, Mg2+, or other divalent cations. The preparation method of the present invention comprises obtaining plasma solution from the body fluid of *Galleria mellonella* larvae, treating the plasma with solvent or buffer solution to produce fractions, and selecting the fraction showing a phenoloxidase activity on peptidoglycan.

In the preparation method, it is preferable to use an anticoagulant buffer solution for obtaining plasma from the body fluid of *Galleria mellonella* larvae. The anticoagulant can be any buffer solution capable of suppressing coagulation of body fluid, and especially citric acid buffer solution is preferred.

The anticoagulating buffer solution further comprises an inhibitor which can irreversibly inhibit a serine protease. The inhibitor of serine protease can be any inhibitor which can irreversibly inhibit serine protease, thereby obtaining phenoloxidase faction from the body fluid of *Galleria mellonella* larvae.

Preferably, the inhibitor can include p-(aminginophenyl)-methanesulfonylfluoride (p-APMSF), phenylmethanesulfonylfluoride (P)MSF), and diisopropylifluorophosphate (DFP). The concentration of inhibitor can be 0.2 mM or more. When obtaining the insect body fluid, the cheating agent can be added to the anticoagulant for inhibiting coagulation of cells, and preventing activation of phenoloxidase system.

For example, a process of treating the plasma sample with solvent or buffer solution in the preparation method can be carried out by a column chromatography.

There is no limitation on solvent or buffer solution used in the separation process. The anticoagulant can be used for obtaining the plasma solution from the insect. Preferably, by adding the cheating agent to the anticoagulant, a desirable phenoloxidase composition can be obtained by inhibiting reactions associated with protein coagulation.

The cheating agent which is sufficient for cheating calcium ion contained in plasma sample and separation processes can include any kind of known cheating agents without limitation, for examples EDTA, EGTA, citric acid, etc. The cheating agent can be used in various amounts, depending on the kind of subject insect, and separation conditions such as the kind of column, and solvent. A preferred amount of cheating agent can be a sufficient amount for cheating Ca2+ contained in separating processes.

Accordingly, a person having an ordinary still in the field can determine a suitable amount of cheating agent without excess experimental efforts.

For example, the treating process of plasma of *Galleria mellonella* larvae with solvent or buffer solution can be carried out by a column chromatography in which the plasma can be loaded on column filled with resin, and eluted with solvent or buffer solution like an anticoagulating buffer solution to produce fractions. Only column chromatography provides a composition for specifically detecting peptidoglycan without complicated purification processes such as affinity chromatography.

The resin used in the column chromatography can be sugars such as monosaccharide or polysaccharide as a support, and preferably includes sugar resins such as agarose or dextran, and vinyl resin. For examples, Sephadex or Toyoperal can be used.

The composition of the present invention can be used for specifically detecting peptidoglycan, and thus can be used for the diagnosis of bacterial infection containing peptidoglycan in cell walls.

Accordingly, the present invention provides a detection method for the presence of peptidoglycan in a sample. The detection method comprises obtaining sample from subject matter, adding a composition showing a phenoloxidase activity on peptidoglycan in the absence of Ca2+, and measuring the phenoloxidase activity of the sample. The composition showing a phenolaxidase activity is intended to include the composition for detecting peptidoglycan. In an specific embodiment of the present invention, the plasma of *Galleria mellonella* larvae can be recovered in the presence of cheating agent with sufficient amount of cheating Ca2+ contained in plasma sample and separating processes, and then, the plasma can be treated with solvent which contains cheating agent in sufficient amount of cheating Ca2+ contained in plasma sample and separating process to produce fractions. A fraction having a phenoloxidase activity on peptidoglycan can be selected by treating the fractions in an absence of Ca2+ to produce the composition of the present invention.

In the detection method of peptidoglycan according to the present invention, the test subject can be those spread in the surroundings, such as animals including human being and live organisms. For example, the detection method includes a diagnosing method for Gram-positive bacteria by obtaining blood from the test subject and detecting peptidoglycan. In another example, it is possible to diagnose the infection of bacteria containing peptidoglycan in cell walls, such as Gram-positive bacteria by obtaining water from the breeding field and detecting peptidoglycan.

As desired, to improve the specificity of diagnosis for bacterial infection, it is possible to remove lipopolysaccharide from the test sample.

For example, it is possible to remove lipopolysaccharide by treating the test sample with agents capable of specifically binding to or precipitating the lipopolysaccharide such as polymyxin before diagnosing.

In the present invention, a conventional method or modified method, which is known as a measuring method of phenoloxidase activity, can be used in measuring the phenoloxidase activity. For example, by using coloring reaction with 4-methylcatechol/4-hydroxyprolineethylester (4-MC/4-HP), or melanin formation reaction with dopamine, the absorbance can be measured to provide phenoloxidase activity as explained below. The presence of peptidoglycan can be easily determined from the measurement of phenoloxidase activity.

In addition, the present invention provides a diagnosis kit for peptidoglycan. The diagnosis kit for peptidoglycan comprises the composition which has a phenoloxidase activity on peptidoglycan in the absence of Ca2+. In the specific embodiment, the composition can be a composition which shows a phenoloxidase activity on peptidoglycan in the absence of Ca2+. Preferably, the composition can be prepared by recovering plasma of *Galleria mellonella* larvae in the presence of cheating agent with sufficient amount of cheating Ca2+ contained in plasma sample and separating process, treating the plasma with solvent which contains cheating agent with sufficient amount of cheating Ca2+ contained in plasma sample and separating process to produce fractions, and selecting a fraction having the phenoloxidase activity on peptidoglycan by treating the fractions without the addition of Ca2+, Mg2+, or other divalent cations.

The following examples are intended to further illustrate the present invention. However, these examples are shown only for better understanding of the present invention without limiting its scope.

EXAMPLE 1

Preparation of Plasma and Hemocyte from *Galleria mellonella* Larva

Larvae among *Galleria mellonella* larva that are about 2.5-3 cm in length were selected and anesthetized on ice for 10-30 minutes. Then, anticoagulant buffer solution (pH 4.6) and 0.2 mM of p-APMSF (Wako Co., Japan) was injected to the second node from the head (5 ml) with a syringe having a 23 G needle. The 4-5 drops of body fluid was obtained by halfway slicing the second node from tail, injecting buffer solution with syringe. The anticoagulant buffer solution contains 15 mM of NaCl, 30 mM of trisodium citrate, 26 mM of citric acid, and 20 mM of EDTA.

50 ml of body fluid was centrifuged at 4° C., 371 xg, for 20 minutes to produce supernatant referred as "plasma", and precipitates referred as "hemocyte".

EXAMPLE 2

Preparation of Plasma Solution 2-1: Pretreatment of Extracted Plasma Solution

Figure 1:
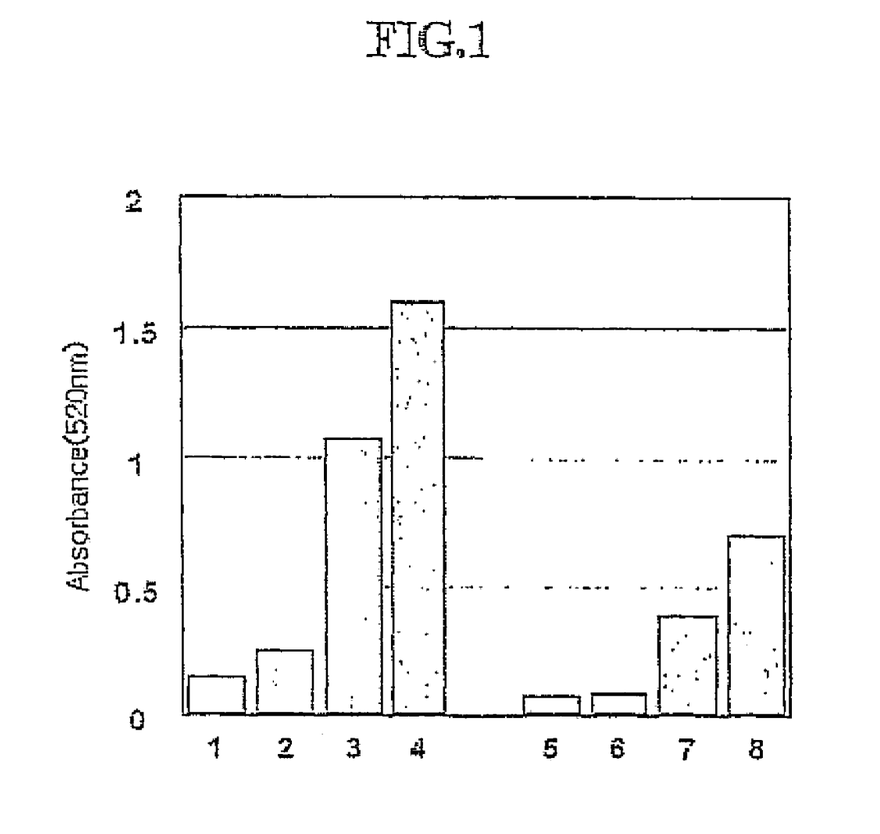
FIG. 1 is a graph showing a phenoloxidase activity on beta-1,3-glucan or peptidoglycan with or without the addition of $Ca^{2+}$.

The plasma solution was treated with an ultra-filtration kit (membrane cut off. 3000) to obtain up to about 2 ml of concentrated plasma solution. In a condition where up to 5 mM of calcium is added to the concentrated solution or no calcium is as to the concentration solution, the phenoloxidase activity of resulting concentrated solutions were measured, and showed in FIG. 1 as follows:

1: plasma solution,
2: plasma solution +1 μg lipopolysaccharide (LPS),
3: plasma solution +1 μg 9 beta-1,3-glucan(BG),
4: plasma solution +1 μg peptidoglycan (PG),
5: plasma solution +Ca2+,
6: plasma solution +1 μg LPS+Ca2+,
7: plasma solution +1/μg BG+Ca2+,
8: plasma solution +1 μg PG+Ca2+.

The plasma solution was used to measure phenoloxidase activities in 1 μg of LPS, peptidoglycan, and beta-1,3-glucan. From the result, the plasma solution of the present invention showed a low phenoloxidase activity on lipopolysaccharide ($2^{nd}$ rod), and a strong phenoloxidase activity on beta-1,3-glucan ($3^{rd}$ rod) and peptidoglycan ($4^{th}$ rod). Also, the system of *Galleria mellonella* larva can be activated in the absence of Ca2+. In fact, it is found that this system is inhibited by the addition of Ca2+.

2-2: Purification of a Fraction Specifically Recognizing Peptidoglycan 1.0×45 of column filed with Sephadex G-100 resin was equalized with anticoagulant buffer solution (pH 5.0). The concentrated sample (500 mg of protein) was loaded on the equalized column, and then, was eluted with anticoagulant at a rate of 3.0 ml per test tube, and the eluted solution was taken to produce 3 ml of 1 to 30 fractions.

Figure 2:
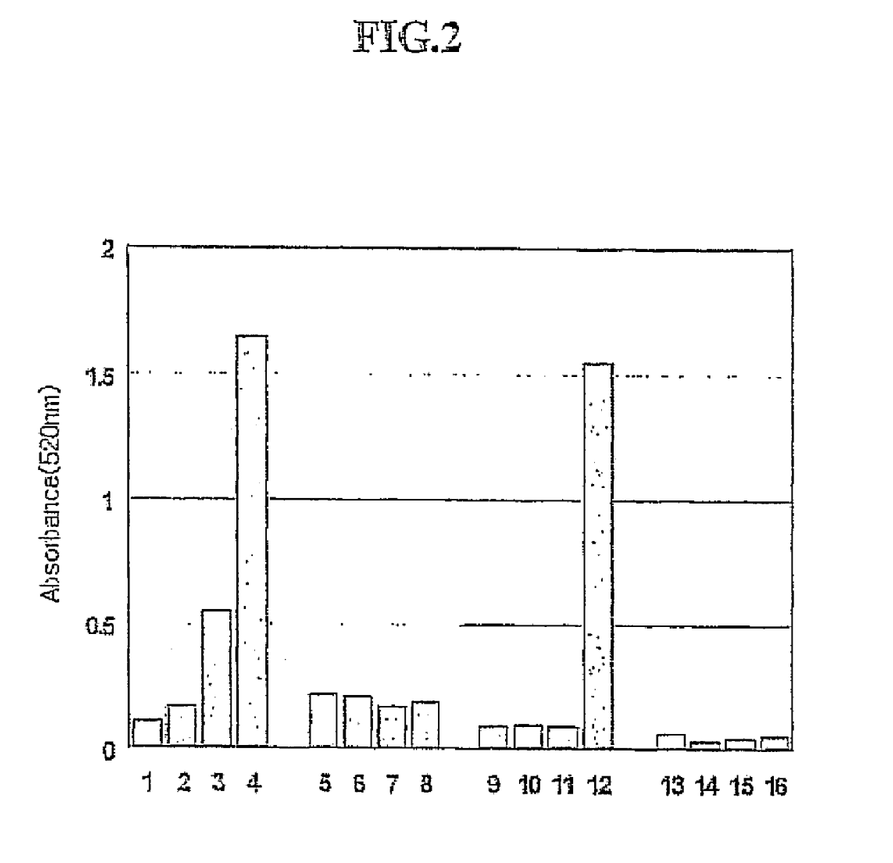
FIG. 2 is a graph showing a phenoloxidase activity of plasma fraction B of *Galleria mellonella* larvae reacted with lipopolysaccharide, beta-1,3-glucan, or peptidoglycan.

Depending on the separation pattern of the proteins, the fractions were divided into Group A (fractions 1~6), Group B (fractions 7~10), and Group C (fractions 11~16). The groups B and C were concentrated with ultra-filtration Kit to be similar concentration of Group A. Before loading, the phenoloxidase activity of the sample, Groups A, B, and C on beta-1,3-glucan, peptidoglycan, and lipopolysaccharide were measured and showed in FIG. 2 as follows:

1: Plasma solution,
2; Plasma solution +1 μg of liposaccharide (LPS).
3: Plasma solution +1 μg of beta-1,3-glucan (BG),
4: Plasma solution +1 μg of peptidoglycan (PG),
5: Group A,
6: Group A+1 μg LPS,
7: Group A+1 μg BG,
8: Group A+1 μg of PG,
9: Group B,
10: Group B+1 μg of LPS,
11: Group B+1 μg of BG,
12: Group B+1 μg of PG,
13: Group C,
14: Group C+1 μg of LPS,
15: Group C+1 μg of BG,
16: Group C+1 μg of PG.

Group B showed a phenoloxidase activity on only the peptidoglycan.

EXAMPLE 3

Phenoloxidase Activity of Plasma Fractions

The group B showed a phenoloxidase activity specifically for peptidoglycan. This example was to test a sensitivity of Group B on peptidoglycan.

Firstly, a peptidoglycan solution was made by suspending 1 mg of water-insoluble peptidoglycan (Fluka Co.) in 20 mM TRIS solution (pH 8.0).

100 μl of the suspension was added to 900 μl of TRIS solution, and then was treated with sonification for a few seconds. 10 μl of the resultant solution was used to measure the phenoloxidase activity.

To measure the phenoloxidase activity, modified Pye's spectrophotometer method was used with 4-methylcatechol and 4-hydroxyproline ethyl ester as a substrate. 1 μg/10 μl of peptidoglycan suspension in TIRS buffer (pH 8.0) was mixed with 30 μl of sample (600 μg of protein amount), and then, incubated at 30° C., for 5 minutes. As a negative control, only 10 μl of 20 mM TRIS buffer solution (pH 8.0) was added. The protein amount in the sample was determined by measuring an absorbance at 280 nm of wavelength, and meant the protein amount in total which were contained in the sample prepared according the above method. Then, 442 μl of 20 mM IRIS buffer (pH 8.0) was poured to test tube, added by 4-MC and 4-HP to be 1 mM, and 2 mM, respectively, and adjusted to 500 μl of volume.

The resultant was incubated at 30° C. for 20 minutes. Then, 100 μl of solution was taken from test tube, diluted with 100 μl of anticoagulant (pH 4.6), and then true phenoloxidase activity was determined by measuring an absorbance of 2 times-diluted phenoloxidase activity at 520 nm of wavelength with a spectrophotometer, and multiplying the absorbance with dilution times.

When measuring the phenoloxidase activity under the condition of calcium addition, 20 mM of TRIS buffer solution (pH 8.0) added by 5.65 mM of $CaCl_2$ was used for determining the phenoloxidase activity according to the substantially same method as explained above.

Figure 3:
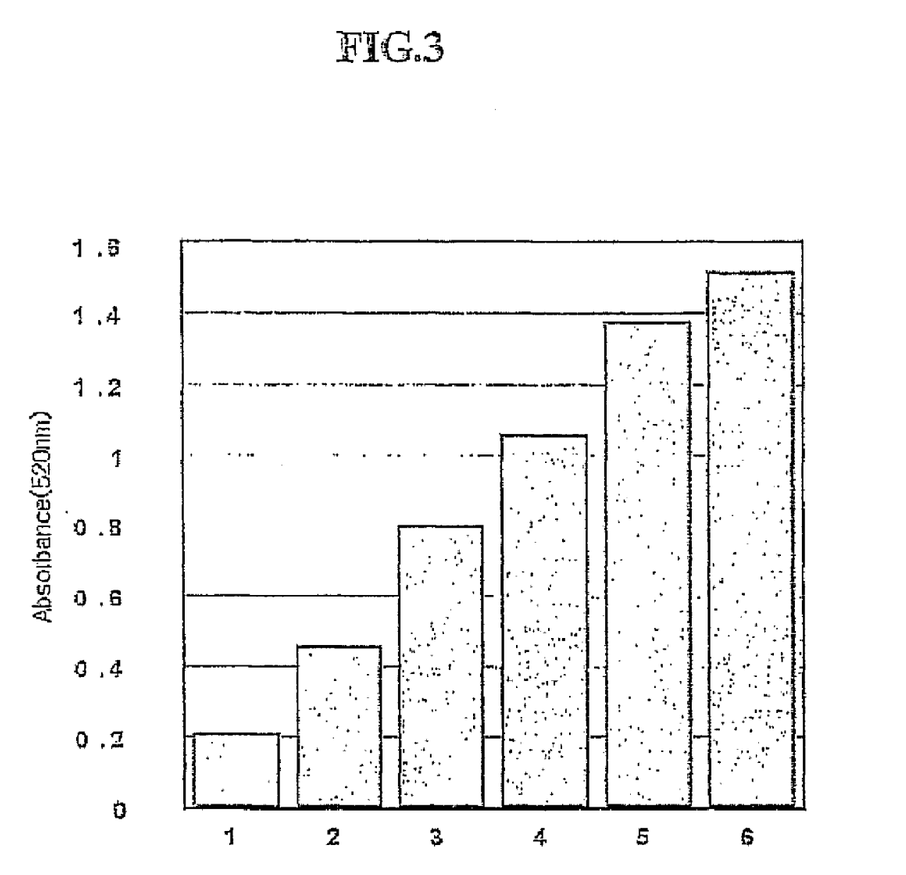
FIG. 3 is a graph showing a phenoloxidase activity of plasma fraction B of *Galleria mellonella* larvae reacted with peptidoglycan in various concentrations.

30 μl of Group B solution prepared according to Example 2 (600 μg of protein amount) was used to determine the phenoloxidase activity depending on the various concentration of water-soluble peptidoglycan without the addition of Ca2+, Mg2+, or other divalent cations; or with the addition of Ca2+. The result was shown in FIG. 3 as follows:

1: Group B,
2: Group B+3 ng of peptidoglycan (PG),
3: Group B+5 ng of PG,
4: Group B+10 ng of PG,
5: Group B+20 ng of PG,
6: Group B+30 ng of PG.

It was confirmed that Group B solution could quantify the peptidoglycan up to 3 ng/ml of concentration.

EXAMPLE 4

Hemocyte Lysate of *Galleria mellonella* Larvae

The hemocytes separated from body fluid as disclosed in Example 1 were added by 50 mM of TIRS buffer (pH 6.5) including 1 mM EDTA as much as half of the volume of hemocyte treated with sonification for 2 minutes, and then, centrifuged at 4° C., 3,586 xg for 20 minutes to produce the supernatant, as called "Primary sample." The precipitate removed from the supernatant was added by TIRS buffer as much as half of the volume of hemocyte, and centrifuged one more time to produce the supernatant, referred as "Second sample." The primary and second samples referred as "hemocyte lysate" were kept in a refrigerator at −80° C. for the following use.

EXAMPLE 5

Phenoloxidase Activity and Specificity of Hemocyte Lysate on Peptidoglycan

Figure 4:
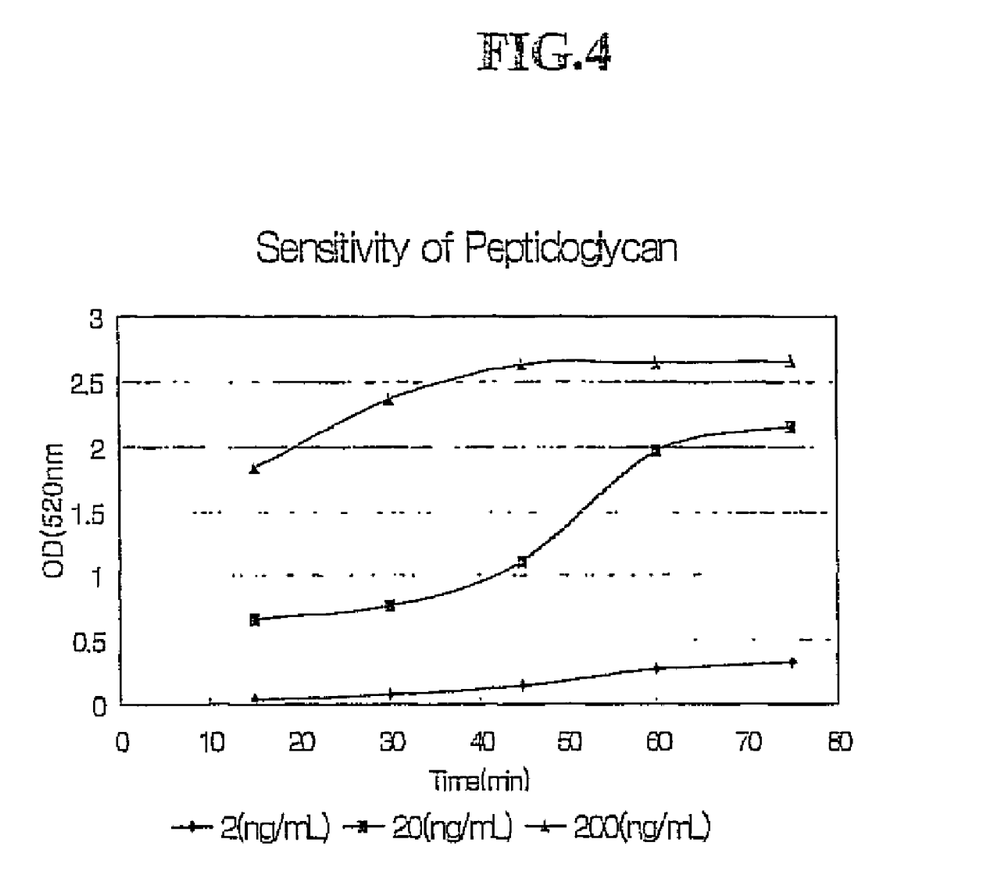
FIG. 4 is a graph showing phenoloxidase activities of plasma fraction B of *Galleria mellonella* larvae, hemocyte lysate, and mixture thereof reacted with beta-1,3-glucan, or peptidoglycan as a substrate.

To determine whether the hemocyte lysate can react with peptidoglycan specifically, the phenoloxidase activity of hemocyte lysate was determined for its activity on beta-1,3-glucan and peptidoglycan, which is shown in FIG. 4. The following solutions were used for this example:

1: Plasma fraction B solution of Example 2 (Protein amount: 200 μg),
2: plasma fraction B solution (200 μg)+beta-1,3-glucan (1 μg),
3: plasma fraction B solution (200 μg)+peptidoglycan (1 μg),
4: hemocyte lysate (protein amount: 100 μg),
5: hemocyte lysate (100 μg)+beta-1,3-glucan (1 μg),
6: hemocyte lysate (100 μg)+peptidoglycan (1 μg), 7: plasma fraction B solution (200 μg)+hemocyte lysate (100 μg),
8: plasma fraction B solution (200 μg)+hemocyte lysate (100 μg)+beta-1,3-glucan (1 μg),
9: plasma fraction B solution (200 g)+hemocyte lysate (100 μg)+peptidoglycan (1 μg)

As a result, when the plasma fraction B solution of Example 2 including anticoagulant (protein amount: 200 μg) was added by 1 μg of beta-1,3-glucan and 1 μg of peptidoglycan, respectively ($2^{nd}$, and $3^{rd}$ rods of FIG. 4), the phenoloxidase activity was not detected. Also, when the hemocyte lysate solution (protein amount: 100 g) was added by 1 μg of beta-1,3-glucan and 1 μg of peptidoglycan, respectively ($5^{th}$, and $6^{th}$ rods of FIG. 4), the phenoloxidase activity was not detected. However, when plasma fraction B solution (protein amount: 200 μg) was added by 100 μg of hemocyte lysate and 1 μg of peptidoglycan ($9^{th}$ rod), the increase in the phenoloxidase activity was detected. However, when plasma fraction B solution (protein amount: 200 μg) was added by 100 μg of hemocyte lysate and 1 μg of beta-1,3-glucan (1 rod), the phenoloxidase activity was not detected.

Accordingly, the mixture of plasma fraction B solution and hemocyte lysate specifically recognized peptidoglycan and showed phenoloxidase activity. In addition, compared with only the plasma fraction B solution, the mixture showed the phenoloxidase activity despite of using a smaller amount of plasma fraction B solution. Thus, it is possible to detect peptidoglycan with a smaller amount of plasma fraction by adding the hemocyte lysate to the plasma fraction.

EXAMPLE 6

Effect of Hemocyte Lysate on Phenoloxidase Activity

After reaction with 30 μg of each solution of Plasma fraction B solution of Example 2 (protein amount: 600 μg), plasma fraction B solution (protein amount: 600 μg)+peptidoglycan (1 μg), plasma fraction B solution (protein amount: 600 μg)+hemocyte lysate (protein amount: 100 μg), plasma fraction B solution (protein amount: 600 μg)+hemocyte lysate (protein amount: 100 μg)+peptidoglycan (1 μg) for 15 minutes, the phenoloxidase activities of the solutions were determined according to Example 3.

Figure 5:
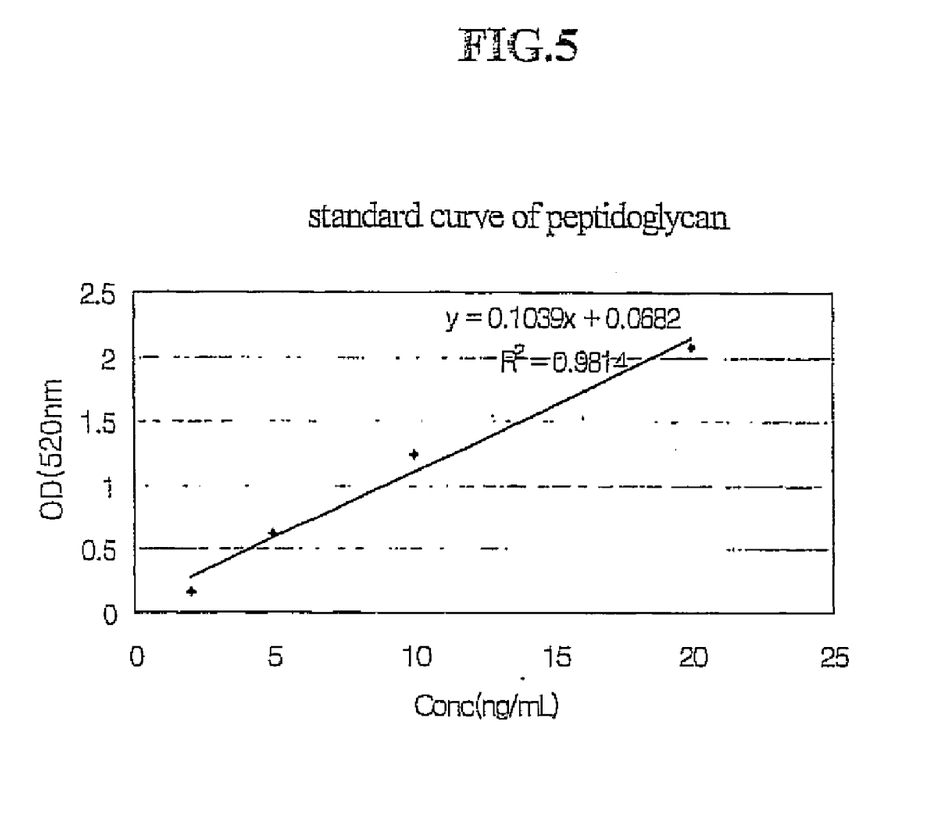
FIG. 5 is a graph showing phenoloxidase activity of solution containing plasma fraction B with protein amount of 600 μg, and hemocyte lysate with protein amount of 200 μg of *Galleria mellonella* larvae which are reacted with peptidoglycan.

The phenoloxidase activity was measured on the solution which was substantially the same as the above solutions except that the plasma fraction B solution of Example 2 (protein amount: 200 μg) was added by anticoagulant. The result was shown in FIG. 5:

1: Plasma fraction B solution (600 μg),
2: Plasma fraction B solution (600 μg)+peptidoglycan (1 μg),
3: Plasma fraction B solution (600 μg)+hemocyte lysate (100 μg),
4: Plasma fraction B solution (600 μg)+hemocyte lysate (100 μg)+peptidoglycan (1 μg),
5: Plasma fraction B solution (200 μg),
6: Plasma fraction B solution (200 μg)+peptidoglycan (1 μg),
7: Plasma fraction B solution (200 μg)+hemocyte lysate (100 μg),
8: Plasma fraction B solution (200 μg)+hemocyte lysate (100 μg)+peptidoglycan (1 μg).

As a result, while the fraction B solution with protein amount of 600 μg showed strong phenoloxidase activity on peptidoglycan ($2^{nd}$ rod), the fraction B solution with protein amount of 200 μg showed low phenoloxidase activity on peptidoglycan ($6^{th}$ rod). Accordingly, the addition of the hemocyte lysate (protein amount: 100 μg) to plasma fraction B solutions increased the phenoloxidase activity, Both the solutions with protein amount of 600 μg and 200 μg had higher phenoloxidase activity ($4^{th}$ and $8^{th}$ rods). Accordingly, it was found that a component contained in hemocyte lysate activated the phenoloxidase specifically.

EXAMPLE 7

Phenoloxidase activity of a composition comprising plasma fraction B solution and hemocyte lysate 30 μl of the solution (protein amount of fraction B: 200 μg, protein amount of hemocyte lysate: 100 μg) containing the plasma fraction B solution added by anticoagulant buffer solution (200 μg of protein amount of plasma fraction B) of Example 2, and the hemocyte lysate prepared-in Example 4 was tested for the phenoloxidase activity on the various concentrations of peptidoglycan. In order to obtain the standard curve, the phenoloxidase activity was determined according to the substantially same method as explained above except that the concentration of peptidoglycan was 2, 5, 10, or 20 μg/ml.

Figure 6:
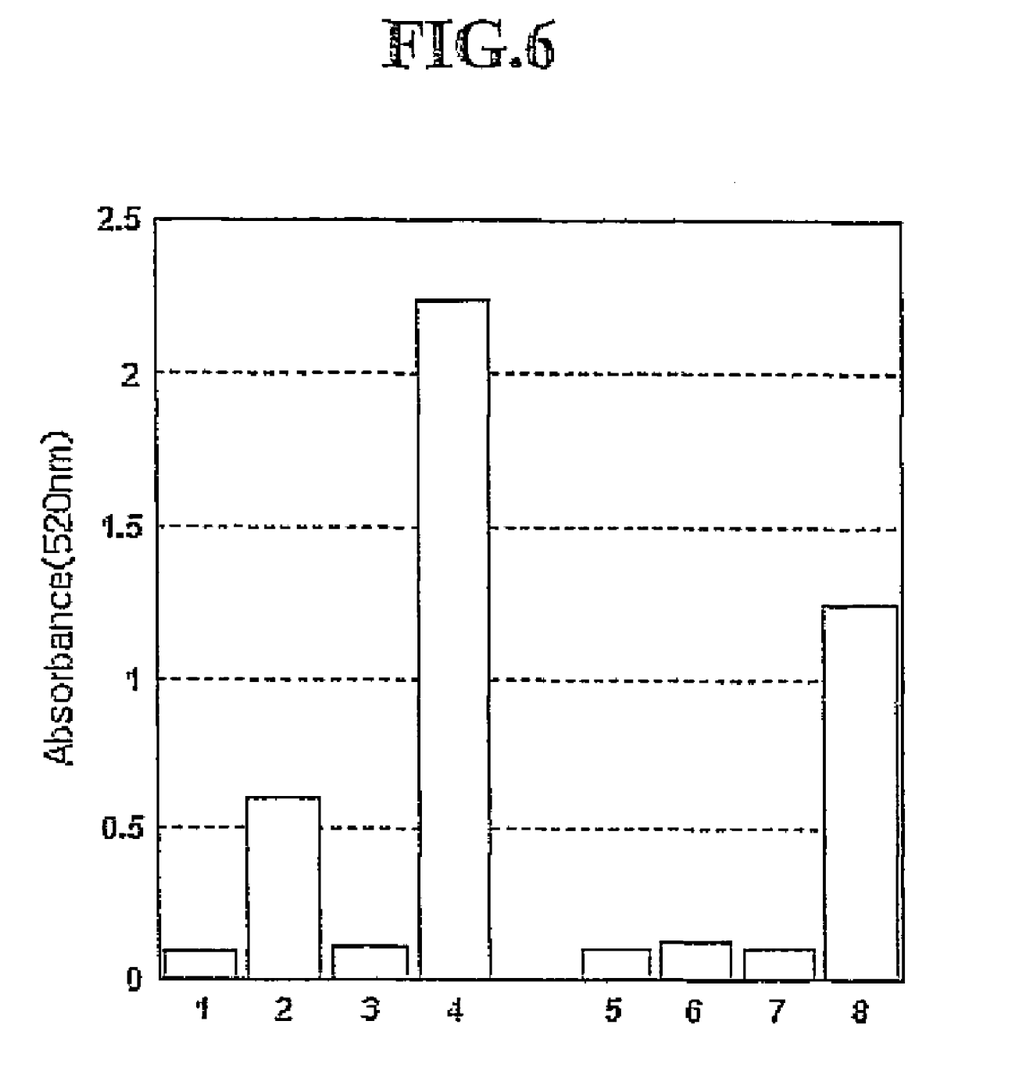
FIG. 6 is a graph showing a phenoloxidase activity of solution containing plasma fraction B and hemocyte lysate of *Galleria mellonella* larvae reacted with peptidoglycan in various concentrations.
Figure 7:
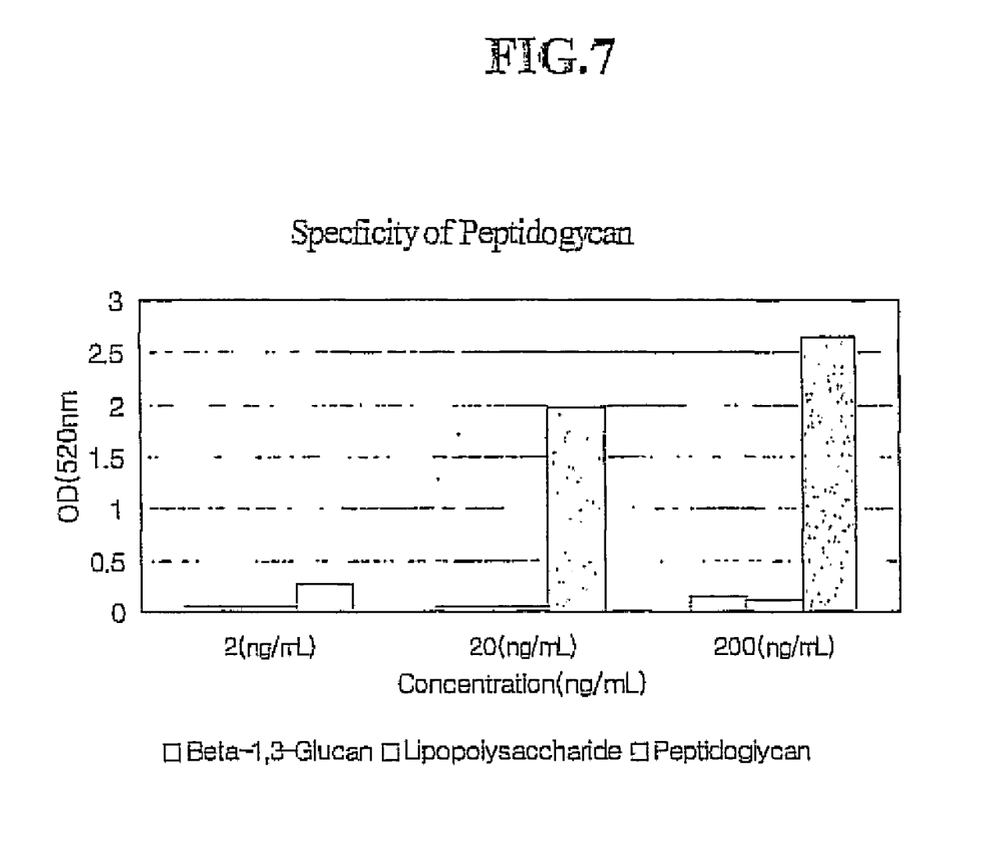
FIG. 7 is a standard curve showing a phenoloxidase activity of solution containing plasma fraction B and hemocyte lysate of *Galleria mellonella* larvae reacted with 20 ng/ml of peptidoglycan.

2 ng/ml, 20 ng/ml, and 200 ng/ml of the peptidoglycan solutions were prepared according to the substantially same method of Example 3, treated with 4-MC/4-HP coloring reaction at 30° C. for 1 hour, and then absorbance at 520 nm was measured. The result of the experiment was shown in FIG. 6, and the standard curve was shown in FIG. 7. As shown in FIG. 7, the correlation constant between the peptidoglycan concentration and the phenoloxidase activity was 0.98, thereby allowing detection of even small amount of peptidoglycan.

EXAMPLE 8

Specificity on Peptidoglycan

To determine whether the plasma fraction B solution of Example 2 (protein amount: 200 μg) and hemocyte lysate (protein amount: 100 μg) have a specificity on peptidoglycan, the phenoloxidase activities on lipopolysaccharide and beta-1,3-glucan were measured on 30 μl of the plasma fraction B solution of Example 2 (protein amount: 200 μg) and hemocyte lysate (protein amount: 100 μg), respectively. 2 μg/ml, 20 μg/ml, and 200 μg/ml of the substrate solutions containing beta-1,3-glucan were prepared by suspending beta-1,3-glucan in 20 mM TRIS buffer solution (pH 7.6). 2 μg/ml, 20 μg/ml, and 200 μg/ml of the substrate solutions containing lipopolysaccharide (LPS) were prepared by suspending lipopolysaccharide (Sigma Co.) in 20 mM TRIS buffer solution (pH 7.6), and then sonicating for 2-3 minutes. The phenoloxidase activities were determined using the beta-1,3-glucan solution and the LPS solution as a substrate according to the method of Example 3. This result was then compared with the experiment where 20 ng/ml of peptidoglycan and was shown in FIG. 8.

Figure 8:
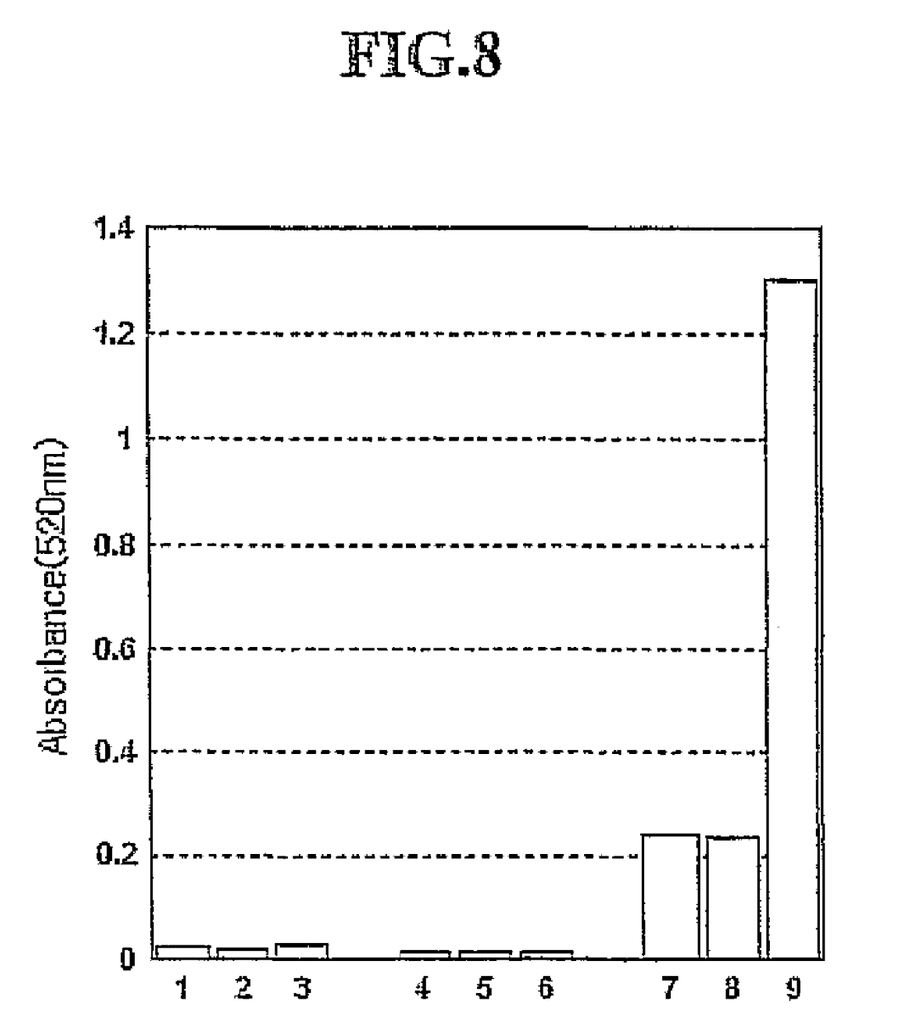
FIG. 8 is a graph showing a phenoloxidase activity of solution containing plasma fraction B and hemocyte lysate of *Galleria mellonella* larvae reacted with lipopolysaccharide, beta-1,3-glucan, or peptidoglycan as a substrate.

As a result, 200 μg/ml of LPS and beta-1,3-glucan solution did not show any phenoloxidase activity despite the reaction time is increased. Thus, it was found that the phenoloxidase composition of the present invention could be used for specific detection of peptidoglycan.

The present invention makes it possible to quantify even a small amount of peptidoglycan contained in human blood, tissue, body fluid, water or food, and to diagnose infection of microorganism having peptidoglycan as a component of cell wall. In addition, the composition can be used as a diagnosis reagent for detecting an infection of Gram-positive bacteria in animal or human being in advance. Therefore, the composition can be used for prevention or treatment of food poisoning and bacterial sepsis.

The invention claimed is:

1. A composition for selectively detecting a peptidoglycan comprising an extract of insect body fluid which has a phenoloxidase activity on the peptidoglycan without the addition of divalent cations to activate the phenoloxidase activity on the peptidoglycan, wherein the extract of insect body fluid comprises a plasma solution and hemocyte lysate of insect body fluid derived from *Galleria mellonella* larvae.

2. The composition according to claim 1, wherein the extract of insect body fluid is a fraction having a phenoloxidase activity on peptidoglycan without the addition of divalent cations to activate a phenoloxidase activity on the peptidoglycan, and the fraction is selected from fractions which are prepared by lysing hemocyte contained in insect body fluid containing plasma and hemocyte of *Galleria mellonella* larva, and treating with solvent or buffer solution.

3. The composition according to claim 2, wherein the solvent or buffer solution comprises a chelating agent in a sufficient amount for chelating calcium ion present in a sample and separation process.

4. The composition according to claim 2, wherein the fraction is a fraction prepared through column chromatography.

5. The composition according to claim 4, wherein the column is filled with a sugar resin or a vinyl resin.

6. The composition according to claim 1, wherein the extract of insect body fluid is a fraction having a phenoloxidase activity on peptidoglycan without the addition of divalent cations to activate a phenoloxidase activity on the peptidoglycan, and the fraction is selected from fractions which are prepared by adding hemocyte lysate or partially-purified hemocyte lysate to fractions obtained by treating plasma of *Galleria mellonella* larvae with solvent or buffer solution.

7. The composition according to claim 6, wherein the solvent or buffer solution comprises a chelating agent in a sufficient amount for chelating calcium ion present in a sample and separation process.

8. The composition according to claim 6, wherein the fraction is a fraction prepared through column chromatography.

9. A method of detecting a peptidoglycan comprising:
obtaining a sample from a test subject;
adding to the sample an extract of insect body fluid which has a phenoloxidase activity on the peptidoglycan without the addition of calcium to activate the phenoloxidase activity on the peptidoglycan, wherein the extract of insect body fluid comprises a plasma solution and hemocyte lysate of insect body fluid derived from *Galleria mellonella* larvae; and
measuring a phenoloxidase activity in the sample for detecting the peptidoglycan.

10. The method according to claim 9, wherein the extract of insect body fluid is a fraction having a phenoloxidase activity on peptidoglycan without the addition of the calcium or other divalent cations to activate a phenoloxidase activity on the peptidoglycan, and the fraction is selected from fractions which are prepared by lysing hemocyte in insect body fluid containing plasma and hemocyte of *Galleria mellonella* larva, and treating with solvent or buffer solution.

11. The method according to claim 10, wherein the solvent or buffer solution comprises a chelating agent in a sufficient amount for chelating divalent cations present in a sample and separation process.

12. The method according to claim 10, wherein the fraction is a fraction prepared through column chromatography.

13. The method according to claim 12, wherein the column is filled with a sugar resin or a vinyl resin.

14. The method according to claim 9, wherein the extract of insect body fluid is a fraction having a phenoloxidase activity on peptidoglycan without the addition of the calcium or other divalent cations to activate a phenoloxidase activity on the peptidoglycan, and the fraction is selected from fractions which are prepared by adding hemocyte lysate or partially-purified hemocyte lysate to fractions obtained by treating plasma of *Galleria mellonella* larvae with solvent or buffer solution.

15. The method according to claim 14, wherein the solvent or buffer solution comprises a chelating agent in a sufficient amount for chelating divalent cations present in a sample and separation process.

16. The method according to claim 14, wherein the fraction is a fraction prepared through column chromatography.

17. The method according to claim 16, wherein the column is filled with a sugar resin or a vinyl resin.

18. A detection kit for peptidoglycan comprising an extract of insect body fluid which has a phenoloxidase activity on the peptidoglycan without the addition of divalent cations to activate the phenoloxidase activity on the peptidoglycan, wherein the extract of insect body fluid comprises a plasma solution and hemocyte lysate of insect body fluid derived from *Galleria mellonella* larvae and instruction for the use thereof to detect the peptidoglycan.

19. The detection kit according to claim 18, wherein the extract of insect body fluid is a fraction having a phenoloxidase activity on peptidoglycan without the addition of the calcium or other divalent cations to activate a phenoloxidase activity on the peptidoglycan, and the fraction is selected from fractions which are prepared by lysing hemocyte in insect body fluid containing plasma and hemocyte of *Galleria mellonella* larva, and treating with solvent or buffer solution.

20. The detection kit according to claim 18, wherein the extract of insect body fluid is a fraction having a phenoloxidase activity on peptidoglycan without the addition of the calcium or other divalent cations to activate a phenoloxidase activity on the peptidoglycan, and the fraction is selected from fractions which are obtained by adding hemocyte lysate or partially-purified hemocyte lysate to fractions obtained by treating plasma of *Galleria mellonella* larvae with solvent or buffer solution.

* * * * *

UNITED STATES PATENT AND TRADEMARK OFFICE
CERTIFICATE OF CORRECTION

PATENT NO. : 7,507,553 B2  
APPLICATION NO. : 11/460406  
DATED : March 24, 2009  
INVENTOR(S) : Bu-Soo Park et al.

Page 1 of 1

It is certified that error appears in the above-identified patent and that said Letters Patent is hereby corrected as shown below:

Column 2, line 25 before "result" insert --a--
Column 4, line 13 replace "factions" with --fractions--
Column 4, line 17 replace "cheating" with --chelating--
Column 4, line 45 replace "faction" with --fractions--
Column 4, line 51 replace "cheating" with --chelating--
Column 4, line 60 replace "cheating" with --chelating--
Column 4, line 63 both occurrences of "cheating" replace with --chelating--
Column 4, line 65 replace "cheating" with --chelating--
Column 4, line 66 replace "cheating" with --chelating--
Column 5, line 2 replace "cheating" with --chelating--
Column 5, line 3 replace "cheating" with --chelating--
Column 5, line 6 replace "cheating" with --chelating--
Column 5, line 35 replace "cheating" with --chelating--
Column 5, line 36 replace "cheating" with --chelating--
Column 5, line 38 replace "cheating" with --chelating--
Column 5, line 39 replace "cheating" with --chelating--
Column 6, line 11 both occurrences of "cheating" replace with --chelating--
Column 6, line 13 replace "cheating" with --chelating--
Column 6, line 14 replace "cheating" with --chelating--
Column 8, line 1 replace "IRIS" with --TRIS--
Column 8, line 36 replace "TIRS" with --TRIS--
Column 8, line 41 replace "TIRS" with --TRIS
Column 9, line 5 replace "200g" with --200µg--
Column 9, line 12 replace "100g" with --100µg--

Signed and Sealed this

Ninth Day of June, 2009

JOHN DOLL  
*Acting Director of the United States Patent and Trademark Office*